US007815912B2

(12) United States Patent
Bunschoten et al.

(10) Patent No.: US 7,815,912 B2
(45) Date of Patent: Oct. 19, 2010

(54) METHOD OF CONTROLLED OVARIAN HYPERSTIMULATION AND PHARMACEUTICAL KIT FOR USE IN SUCH METHOD

(75) Inventors: Evert Johannes Bunschoten, Heesch (NL); Herman Jan Tijmen Coelingh Bennink, Driebergen (NL)

(73) Assignee: Ares Trading, S.A., Aubonne (CH)

( * ) Notice: Subject to any disclaimer, the term of this patent is extended or adjusted under 35 U.S.C. 154(b) by 780 days.

(21) Appl. No.: 10/517,028

(22) PCT Filed: Jun. 6, 2003

(86) PCT No.: PCT/NL03/00370

§ 371 (c)(1),
(2), (4) Date: Jun. 15, 2005

(87) PCT Pub. No.: WO03/103770

PCT Pub. Date: Dec. 18, 2003

(65) Prior Publication Data

US 2005/0235374 A1    Oct. 20, 2005

(30) Foreign Application Priority Data

Jun. 7, 2002    (EP) ................................. 02077221

(51) Int. Cl.
*C07K 14/59*    (2006.01)
*A61K 38/24*    (2006.01)
(52) U.S. Cl. ......................... 424/198.1; 530/398; 514/8
(58) Field of Classification Search ....................... None
See application file for complete search history.

(56) References Cited

U.S. PATENT DOCUMENTS

| 6,585,982 | B1 * | 7/2003 | Grøndahl et al. ............ 424/400 |
| 7,341,989 | B2 * | 3/2008 | Hillier et al. .................... 514/2 |
| 2003/0092628 | A1 * | 5/2003 | de Greef et al. ................ 514/12 |
| 2006/0217315 | A1 | 9/2006 | Coelingh Bennink et al. |

FOREIGN PATENT DOCUMENTS

| EP | 0 788 799 A2 | 8/1997 |
| WO | WO 98/58657 | 12/1998 |
| WO | WO 99/55357 | 11/1999 |
| WO | WO 01/00227 | 1/2001 |

OTHER PUBLICATIONS

Hideyuki Ikenaga, The Clinical Significance of the Ratio in FSH/LH of Human Menopausal Gonadotropins in a Programmed Stimulation Regimen for IVF-ET, Acta Obst. Gynaec, JPH, 1995, vol. 47, No. 11, pp. 1223-1229 (with translation).*
Christina Bergh, Recombinant Follicle Stimulating Hromone, Hum. Reprod., 1999, vol. 14, No. 6, pp. 1418-1419.*
Scott, et al., Correlation of Follicular Diameter with Oocyte Recovery and Maturity at the Time of Transvaginal Follicular Aspiration, Journal of in Vitro Fertilization and Embryo Transfer, 1989, vol. 6, No. 2, pp. 73-75.*
International Search Report of Int. Appln. No. PCT/NL2003/000370.
Al-Inany, H., et al., "GnRH Antagonist in Assisted Reproduction: a Cochrane Review," Human Reproduction, vol. 17, No. 4, pp. 874-885 (2002).
Burgues, S., et al., "The Effectiveness and Safety of Recombinant Human LH to Support Follicular Development Induced by Recombinant Human FSH in WHO Group I Anovulation: Evidence from a Multicentre Study in Spain," Human Reproduction, vol. 16, No. 12, pp. 2525-2532 (2001).
Fauser, B., et al., "Endocrine Profiles after Triggering of Final Oocyte Maturation with GnRH Agonist after Cotreatment with the GnRH Antagonist Ganirelix during Ovarian Hyperstimulation for in vitro Fertilization," The Journal of Clinical Endocrinology and Metabolism, vol. 87; No. 2, pp. 709-715 (2002).
Krusche, C., et al., "The Progesterone Antagonist Onapristone Retards the Advanced Endometrial Transformation after Gonadotropin Stimulation in Rabbits," Steroids, vol. 65, pp. 773-782 (2000).
Lisi, F., et al., "Use of Recombinant Follicle-Stimulating Hormone (Gonal F) and Recombinant Luteinizing Hormone (Luveris) for Multiple Follicular Stimulation in Patients with a Suboptimal Response to in vitro Fertilization," Fertility and Sterility, vol. 79, No. 4, pp. 1037-1038 (Apr. 2003).

(Continued)

*Primary Examiner*—Lorraine Spector
(74) *Attorney, Agent, or Firm*—Howrey LLP

(57) ABSTRACT

One aspect of the present invention is concerned with a method of controlled ovarian hyperstimulation in a mammalian female, said method comprising the co-administration to said female of —a substance having follicle stimulating hormone activity (FSH substance) in an amount effective to stimulate multiple follicular development; —gonadotropin releasing hormone (GnRH) antagonist in an amount equivalent to a daily subcutaneous dose of at least 0.5 mg ganirelix to prevent a premature LH-surge; and —a LH substance in an amount effective to prevent or suppress symptoms of luteinising hormone (LH) deficiency resulting from the administration of the GnRH antagonist; followed by administering a meiosis and luteinisation inducing substance (ML substance) in an amount effective to stimulate resumption of meiosis and luteinisation, and wherein the LH substance is not obtained from the urine of human females. Another aspect of the to invention relates to a pharmaceutical kit for use in a method of controlled hyperstimulation, which kit comprises: —at least one parenteral or oral dosage unit containing one or more FSH substances in an amount equivalent to a subcutaneous dose of 50-1500 I.U. FSH; —at least one parenteral dosage unit containing one or more GnRH antagonists in an amount equivalent to a subcutaneous dose of 0.5-25 mg ganirelix; —at least one parenteral dosage unit containing one or more LH substances in an amount equivalent to a subcutaneous dose of 50-3000 I.U. recombinant LH; wherein the LH substance is not obtained from the urine of human females.

13 Claims, No Drawings

OTHER PUBLICATIONS

Ludwig, M., et al., "Developments in Drugs for Ovarian Stimulation," Best Practice & Research Clinical Obstetrics & Gynaecology, vol. 17, No. 2, pp. 231-247 (2003).

Ron-El, R., et al., "Induction of Ovulation after GnRH Antagonists," Human Reproduction Update 2000, *European Society of Human Reproduction and Embrology*, vol. 6, No. 4, pp. 318-321 (2000).

Wikland, M., et al., "A Prospective, Randomized Comparison of Two Starting Doses of Recombinant FSH in Combination with Cetrorelix in Women Undergoing Ovarian Stimulation for IVF/ICSI," Human Reproduction, *European Society of Human Reproduction and Embrology*, vol. 16, No. 8, pp. 1676-1681 (2001).

* cited by examiner

METHOD OF CONTROLLED OVARIAN HYPERSTIMULATION AND PHARMACEUTICAL KIT FOR USE IN SUCH METHOD

FIELD OF THE INVENTION

The present invention is concerned with a method of controlled ovarian hyperstimulation in mammalian females. More particularly the invention relates to a method of controlled ovarian hyperstimulation for treating infertility in mammals, which method comprises the administration to a mammalian female of a substance having follicle stimulating hormone activity (FSH substance) in an amount effective to stimulate multiple follicular development and of a gonadotropin releasing hormone (GnRH) antagonist in an amount sufficient to prevent the occurrence of a premature LH surge, followed by the administration of a meiosis and luteinisation inducing substance (ML substance) in an amount effective to stimulate resumption of meiosis and luteinisation.

Another aspect of the invention is concerned with a pharmaceutical kit for use in the present method of controlled ovarian hyperstimulation.

BACKGROUND OF THE INVENTION

The ovarian function of mammalian females is regulated by pituitary hormones, called gonadotropins. The best known gonadotropins are follicle stimulating hormone (FSH), which causes follicle maturation, and luteinising hormone (LH), which causes ovulation.

After each menses the ovaries are stimulated by FSH released by the pituitary to grow a cohort of follicles. These follicles each comprise an oocyte (egg cell) which is enveloped by an orb of granulosa cells. During growth of the follicles several layers of granulosa cells are being formed. Gradually, one follicle becomes dominant and the others become atretic and degenerate by apoptosis. Follicle maturation during the normal menstrual cycle occurs in 12-14 days. As the number of granulosa cells increases, more estrogen is secreted by these cells.

Once the dominant follicle has reached maturity, the follicle will burst (ovulate) under the action of a surge of LH which is released by the pituitary in response to the increased blood serum estrogen level (positive feedback). The oocyte is discharged from the follicle into the ampulla of the Fallopian tube, where fertilization may take place. The oocyte or embryo is transported to the uterus in 5-7 days, where implantation may occur in the midluteal phase.

The follicle which has discharged the oocyte is transformed into a new hormone producing organ, the corpus luteum. The corpus luteum produces progesterone together with estrogens. The corpus luteum has a limited lifespan of about 12-14 days. After said period, it ceases to function, and as a result the blood level of estrogens and progesterone drops. This decline of progesterone causes necrosis of the lining of the uterus and thus menstruation.

In particular in the area of ovulation induction, the past decades have shown the development and commercial introduction of numerous drugs assisting in fertility management of infertile couples. Amongst others, these include anti-estrogens (like clomiphene citrate and tamoxifen citrate), pulsatile GnRH, purified and recombinant gonadotropins, and GnRH agonists and antagonists. The specific drugs used and administration regimens chosen largely depend on the goal of the treatment, e.g. induction of mono-ovulation in anovulatory females or controlled ovarian hyperstimulation (COH) to induce multiple follicular development as an element in assisted reproductive technologies (ART). Examples of ART methods that are widely used to treat female and/or male factor infertility include intrauterine insemination (IUI) and in vitro fertilization (IVF). IVF can be performed with and without intracytoplasmatic sperm injection (ICSI) and includes a subsequent embryo transfer step.

COH is nowadays widely used in ART. First results with COH were disappointing as a result of the occurrence of premature LH surges in about 30% of the cases. Such a premature LH-surge may incite ovulation of oocytes which have not yet reached maturity and/or it may frustrate harvesting of oocytes for in vitro fertilisation (IVF). It was found that the introduction of GnRH agonists allowed the prevention of premature LH surges as well as programming of the treatment cycles. To date GnRH agonists are used in most of the cycles. However, GnRH agonists are inconvenient (long treatment period), may induce ovarian cysts, are expensive and not devoid of adverse effects (side effects, increased incidence of Ovarian HyperStimulation Syndrome (OHSS), etc.).

Recently GnRH antagonists were introduced to prevent premature LH surges and to avoid the problems related to the use of GnRH agonists. WO 98/58657 (AKZO NOBEL) suggests that a daily dose of between 0.125 mg and 1 mg ganirelix prevents premature LH rises to occur and at the same time maintains sufficient LH to support follicular maturation and estrogen biosynthesis. Likewise CN 1 199 642 (ASTA Medica) describes the daily subcutaneous administration of cetrorelix in an amount of 0.1-0.5 mg to selectively suppress the secretion of LH.

However, there are concerns about the pregnancy rates observed with protocols using GnRH antagonists. Several studies have indicated that pregnancy rates for GnRH antagonists are lower than those achieved with GnRH agonists. WO 01/00227 (AKZO NOBEL) which was published recently, reports that it has been found that there is no relationship between the implantation rate and level of LH, but that there exists a relationship between the GnRH antagonist levels and implantation rate. It is advocated in said application to administer GnRH antagonist in an amount depending on the body weight. The advocated levels are between 128 and 264 µg per day.

From the above it will be evident that the successful use of GnRH antagonist depends on accurately establishing the adequate dose to effectively prevent an LH-surge without lowering endogenous LH-levels too much. Since the adequate dose is very much dependent on individual physiological attributes, such as bodyweight, the use of a fixed dosage for all females is bound to lead to premature LH-surges in some of them, and bad implantation and pregnancy rates in others. This means that in order to achieve high success rates of treatment, it is necessary to adjust dosages on an individual basis. However, individual adjustment of the dosage levels as proposed in WO 01/00227 has the disadvantage that self administration is no longer an option, or that an assortment of dosage units containing different amounts of GnRH-antagonist is required.

Thus, there is a need for a robust COH method that employs a GnRH antagonist and that performs at least as well as similar methods using GnRH agonists, in terms of prevention of LH-surges and implantation and pregnancy rates.

SUMMARY OF THE INVENTION

The inventors have found that the aforementioned objective may be realised by a COH protocol which comprises the co-administration of a FSH substance to stimulate multiple follicular development, a relatively high dosage of a GnRH antagonist (equivalent to a subcutaneous dose of at least 0.5 mg ganirelix) to secure the prevention of a premature LH-surge and a LH substance. The co-administration of the LH substance was found to enable the administration of GnRH antagonist at elevated dosage levels without any adverse effects on e.g. implantation or pregnancy rates. In addition, the administration of higher dosages of GnRH antagonist was found to provide better prevention of premature LH-surges.

Another important benefit of the combined administration of a relatively high dose of GnRH antagonist and an LH substance resides in the fact that it is possible to formulate a medicament which will produce good results in females with very different physiology. Thus it is possible to develop a single pharmaceutical kit which can suitably be employed in the effective treatment of infertility, irrespective of the female's physiological features. Whereas known COH-protocols that employ GnRH antagonists are bound to lead to premature LH-surges in some females (e.g. with high body weight) or to too much suppression of endogenous LH in other females, the present method is much more robust. Consequently, the present method scores better in terms of ongoing pregnancy rates than existing COH-protocols that employ GnRH antagonists.

DETAILED DESCRIPTION OF THE INVENTION

Thus, one aspect of the present invention is concerned with a method of controlled ovarian hyperstimulation in a mammalian female, said method comprising the co-administration to said female of:

a substance having follicle stimulating hormone activity (FSH substance) in an amount effective to stimulate multiple follicular development;

gonadotropin releasing hormone (GnRH) antagonist in an amount equivalent to a daily subcutaneous dose of at least 0.5 mg ganirelix to prevent a premature LH-surge; and a LH substance in an amount effective to prevent or suppress symptoms of luteinising hormone (LH) deficiency resulting from the administration of the GnRH antagonist;

followed by administering a meiosis and luteinisation inducing substance (ML substance) in an amount effective to stimulate resumption of meiosis and luteinisation, and wherein the LH substance is not obtained from the urine of human females.

Urine of females, particularly of postmenopausal females, contains elevated levels of FSH and LH. FSH has been isolated from female urine for use in COH methods. In principle LH could also be isolated from female urine. However, urine LH is not suitable for use in the present method as it is metabolised extremely quickly. Consequently the LH substance used in the present method is not obtained from the urine of human females.

The term "FSH substance" as used herein, encompasses substances that display a similar functionality as FSH, as well as substances which are capable of triggering the pituitary release of FSH. Similarly the term "ML substance" encompasses substances that display a similar functionality as LH, as well as substances which are capable of triggering the pituitary release of LH. The term "LH substance" refers to substances that display a similar functionality as LH. Consequently, the group of LH substances does not encompass substances that do not have a similar functionality as LH, but which can trigger the pituitary release of LH.

The term female, whenever referred to in here, relates to mammalian females. Preferably the mammalian female is a homo sapiens. For homo sapiens females are usually biologically capable of child bearing between the age of 12 and 55.

The present COH-method is advantageously employed as part of an IVF-protocol. Consequently, in a preferred embodiment, the present method additionally comprises the sequential steps of:

harvesting one or more ova from mature ovarian follicles;
fertilising one or more ova in vitro;
transferring the resulting embryo into the uterus of a mammalian female.

The embryo may be transferred into the female uterus during the same cycle in which the COH-protocol is applied and the one or more ova are harvested, but it is also possible to transfer the embryo in a subsequent cycle. Due to the administration of the LH substance, however, the present method enables high implantation rates when the COH-protocol and embryo transfer occur within the same cycle. Hence, in a particularly preferred embodiment, the controlled ovarian hyperstimulation and transfer of the embryo are carried out within one cycle.

The co-administration of the LH substance in accordance with the present invention serves the purpose of preventing LH deficiency (less than 1 I.U. per liter of blood serum) in the female undergoing treatment. Hence the benefits of the present invention are particularly appreciated when the administration of the FSH substance and GnRH antagonist, without the LH substance, would reduce the female's blood serum LH level to below 1 I.U./liter, preferably to below 0.5 I.U./liter.

In a preferred embodiment of the invention the LH substance is administered in an amount effective to maintain the females blood serum concentration of LH substances (endogenous and exogenous) at a level equivalent to or more than 1 I.U. LH/liter, preferably at more than 1.2 I.U. LH/liter. LH substances that may suitably be employed in the present method include recombinant LH (recLH), chimaeric or otherwise modified gonadotropins with LH-activity, low molecular weight compounds with LH activity and mixtures thereof.

In order to prevent symptoms of LH deficiency the LH substance is suitably administered in a daily dose which is equivalent to a subcutaneous dose of at least 1 I.U., preferably at least 1.4 I.U., more preferably at least 1.7 I.U and most preferably at least 2 I.U. recombinant LH per kg of bodyweight. Usually the maximum daily amount in which the LH substance is administered does not exceed the equivalent of a subcutaneous dose of 40. I.U. per kg of bodyweight. Preferably said maximum daily amount does not exceed the equivalent of a subcutaneous dose of 25 I.U. per kg of bodyweight, more preferably it does not exceed the equivalent of a subcutaneous dose of 15 I.U. per kg of bodyweight.

The FSH substance is preferably administered in an amount equivalent to a daily subcutaneous dose of 1 to 15 I.U. FSH per kg bodyweight.

Best results are obtained with the present method if the GnRH antagonist is administered in a sufficiently high dose to achieve prevention of premature LH surges in virtually all females receiving the treatment. Thus, in a preferred embodiment, the GnRH antagonist is administered in an amount equivalent to a daily subcutaneous dose of at least 0.6 mg ganirelix, more preferably of at least 0.8 mg ganirelix and most preferably of at least 1.0 mg ganirelix. Generally, the GnRH antagonist is administered in an amount that does not exceed the equivalent of a daily subcutaneous dose of 4.0 mg. Preferably said amount does not exceed the equivalent of a daily subcutaneous dose of 3.0 mg, more preferably it does not exceed the equivalent of a daily subcutaneous dose of 2.5 mg.

It is crucial that administration of the GnRH antagonist is started sufficiently early to minimise the chance of a premature LH-surge. A reliable indicator of the chance of the occurrence of a premature LH-surge is the size of the developing ovarian follicle, and in particular the size of largest of these developing follicles. Preferably, the GnRH antagonist is administered at least during the period starting with the moment when the largest developing ovarian follicle has reached an average diameter of 14 mm, preferably of 12 mm, most preferably 10 mm and ending one day prior to the administration of the ML substance in an amount effective to stimulate resumption of meiosis and luteinisation.

To achieve the desired effect on endometrium histology, the GnRH antagonist is administered at least during the period commencing either 6 days after the start of administration of the FSH substance, or at least 4 days prior to the administration of the ML substance in an amount effective to stimulate resumption of meiosis and luteinisation, whichever is the earliest, and ending one day prior to said administration of the ML substance.

In order to effectively compensate the LH-lowering effect of the GnRH antagonist the administration of the LH substance should commence immediately or shortly after the administration of the GnRH antagonist has started and should be continued for as long as the GnRH antagonist is administered. Preferably the LH substance is administered at least during the period commencing 2 days after the start of administration of the GnRH antagonist and ending with the discontinuation of the administration of the GnRH antagonist. More preferably the LH substance is co-administered with the GnRH antagonist throughout the treatment.

The FSH substance is suitably administered at least during the period starting 8 days after the female's spontaneous menses until the day before administration of the ML substance. More preferably the administration of the FSH-substance is commenced no later than 6 days after the female's menses even more preferably on the second day after the menses.

In principle, the present method may suitably employ any GnRH antagonist known in the art. Examples of suitable GnRH antagonists include ganirelix, cetrorelix, a precursor of ganirelix, a precursor of cetrorelix, antagonistic linear peptide analogs of LH releasing hormone (e.g. as described in U.S. Pat. Nos. 5,140,835 and 5,171,835), cyclic hexapeptide derivatives (as described in JP-A 61 191698) and bicyclic peptide derivatives (as disclosed in J. of Medic. Chem. (1993), 36, 3265-73), or mixtures thereof. Preferably the GnRH-antagonist employed in the present method is selected from the group consisting of ganirelix, cetrorelix and mixtures thereof.

The present COH method employs a LH substance to prevent symptoms of LH deficiency, followed by a high (single) dose of a ML substance to stimulate meiosis and luteinisation after the lead follicle has reached maturity and administration of FSH and GnRH antagonist is discontinued. The objective of administering the ML substance at this stage of the cycle is to mimic the LH surge which occurs during the normal menstruation cycle and which induces resumption of meiosis, luteinisation and ovulation. Next to LH a wide range of other pharmaceutical substances may be used to trigger such responses. Preferably the ML substance used in the present method is selected from the group consisting of recombinant LH, urinary choriotropin gonadotropin (uCG), recombinant CG, gonadotropin releasing hormone (GnRH), GnRH agonists and other substances capable of stimulating the release of LH by the pituitary, chimaeric or otherwise modified gonadotropins with LH-activity, low molecular weight compounds with LH activity and mixtures thereof. More preferably the ML substance is selected from recombinant LH, urinary choriotropin gonadotropin (uCG), recombinant CG, gonadotropin releasing hormone (GnRH) and mixtures thereof. Most preferably, the ML substance used to stimulate resumption of meiosis and luteinisation is recLH or uCG.

The amount of ML substance administered in accordance with the present method preferably exceeds an amount which is equivalent to a subcutaneous dosage of at least 2,000 I.U. urinary chorionic human gonadotropin (uhCG), more preferably said amount is equivalent to a subcutaneous dose of 5,000-10,0000 I.U. uhCG. Preferably the ML substance is administered in a single oral or parenteral dose. Most preferably the ML substance is administered subcutaneously or orally.

Throughout this document, the term "parenteral administration" encompasses all modes of administration, requiring injection, implantation or topical administration, except for the oral/intestinal route. Suitable examples of parenteral administration include intramuscular, intravenous, subcutaneous, intravaginal, transdermal and intranasal administration.

As observed herein before, it is well known that both FSH and LH may be isolated from female urine. LH isolated from urine is less suitable for use in the present method as it has a very short in vivo half-life ($t_{1/2}$: 10-20 minutes) and is metabolised very quickly. LH obtained from a recombinant cell line (recLH) is much more stable ($t_{1/2}$: 12-13 hours). Consequently, in a particularly preferred embodiment, the LH substance used to prevent or suppress symptoms of LH deficiency is obtained from a recombinant cell line.

The FSH substance used in the present method may suitably be selected from the group consisting of recombinant FSH (recFSH), urinary FSH (uFSH), agonistic FSH muteins and/or heterocyclic low molecular weight compounds (less than 600 dalton) displaying FSH agonistic activity. Preferably the FSH substance is recFSH or uFSH. Although FSH of urinary origin performs almost equally well as recFSH, it is noted that the isolation of active principles from bodily fluids is associated with lower purity, less product consistency and the risk of transfer of diseases. Hence, in a more preferred embodiment, the FSH substance is FSH obtained from a recombinant cell line.

The primary aim of the co-administration of the LH substance in the present method is to prevent LH deficiency, in particular with the objective of achieving high implantation rates, i.e. implantation rates which are at least as good as those obtained with GnRH agonists. Hence, in a preferred embodiment, the present method is used to treat females wherein the LH deficiency is such that it adversely affects the implantation of the embryo.

Best results are obtained with the present COH-method if the FSH substance and the LH substance are administered at least once daily. Preferably also the GnRH antagonist is administered at least once daily. The preferred mode of administration is parenteral, more preferably subcutaneous.

Another aspect of the present invention relates to a pharmaceutical kit for use in a method of controlled hyperstimulation, which kit comprises:

at least one parenteral or oral dosage unit containing one or more FSH substances in an amount equivalent to a subcutaneous dose of 50-1500 I.U. FSH;

at least one parenteral dosage unit containing one or more GnRH antagonists in an amount equivalent to a subcutaneous dose of 0.5-25 mg ganirelix;

at least one parenteral dosage unit containing one or more LH substances in an amount equivalent to a subcutaneous dose of 50-3000 I.U. recombinant LH;

wherein the LH substance is not obtained from the urine of human females. The aforementioned dosage units containing FSH substance, GnRH antagonist or LH substance may be assembled as separate dosage units, or they may be combined into 2 or even a single dosage unit.

In a preferred embodiment the dosage units in the present kit are designed for at least once daily administration, containing the one or more FSH substance in an amount equivalent to a subcutaneous dose of 100-1200 I.U. FSH, the one or more GnRH antagonists in an amount equivalent to a subcutaneous dose of 0.5-4 mg ganirelix, and the one or more LH substances in an amount equivalent to a subcutaneous dose of 100-1000 I.U. More preferably the kit comprises a dosage unit containing the one or more GnRH antagonists in an amount equivalent to a subcutaneous dose of at least 0.6 mg ganirelix, more preferably of at least 0.8 mg ganirelix, even more preferably of at least 1.0 mg ganirelix and most preferably at least 1.1 mg ganirelix. The latter dosage units preferably contain the one or more GnRH antagonist in an amount that does not exceed the equivalent of a subcutaneous dose of 3 mg ganirelix, more preferably an amount that does not exceed the equivalent of a subcutaneous dose of 2.5 mg ganirelix.

The present kit may additionally contain a single parenteral or oral dosage unit containing one or more ML substances in an amount equivalent to a subcutaneous dose of at least 2,000 I.U. uhCG, preferably equivalent to a subcutaneous dose of 5,000-10,000 I.U. uhCG. In another preferred embodiment of the present kit, the dosage units containing one or more FSH substance, the dosage unit containing one or more GnRH antagonists and the dosage unit containing one or more LH substances are combined in a cartridge for once daily subcutaneous self-administration.

Preferably all the dosage units within the present kit are parenteral dosage units. Furthermore, the parenteral dosage units in the kit are preferably suited for intramuscular or subcutaneous administration.

The present invention is further illustrated by the following examples, which, however, are not to be construed as limiting. The features disclosed in the foregoing description, in the following examples and in the claims may, both separately and in any combination thereof, be material for realising the invention in diverse forms thereof

EXAMPLES

Example 1

An open-label, controlled clinical trial is performed to investigate the efficacy, safety, and tolerability of premature endogenous LH-surge prevention in 90 female subjects undergoing COH and subsequent IVF and embryo transfer (ET), using daily subcutaneous administration, from day 6 of recombinant FSH treatment up to and including the day of urinary hCG treatment, of 0.25 mg cetrorelix (30 subjects), 2.0 mg cetrorelix (30 subjects) or 2.0 mg cetrorelix combined with 400 I.U. recLH (30 subjects).

Although this treatment is suitable for all types of IVF patients (e.g. within the age range 18 to 45 years, with or without displaying polycystic ovarian syndrome and with or without a regular cycle), the following selection criteria are set forth in the investigation: healthy female partners of infertile couples; age at the time of screening between 20 and 39 years; a regular menstrual cycle, and willing to give a written informed consent. However, no special precautions concerning body weight or body mass index are taken.

Prior to the first administration of recombinant FSH a blood sample is taken for hormone analysis (estradiol and LH) and a standard urinary hCG assay is performed to exclude pregnancy. Recombinant FSH treatment is started at day 2 or 3 of menses by a daily subcutaneous injection until the day of hCG administration. During the first 5 days of recombinant FSH treatment the daily dose is fixed to 150 IU. Starting at day 6, blood samples for hormone analysis are taken once every two days prior to drug administration and ultrasonographic monitoring of follicle growth is performed to adjust, if necessary, the daily injectable doses of recombinant FSH.

A subcutaneous injection with urinary hCG (10,000 IU) is administered, when at least three follicles exceed a diameter of 17 mm as measured by ultrasound scan and subsequently oocyte retrieval is performed typically 30-36 hours later.

A daily subcutaneous dosage of 2.0 mg cetrorelix (with or without 400 I.U. recLH) is found to be more efficacious in preventing a premature LH-rise than a subcutaneous dosage of 0.25 mg. This effectiveness is especially apparent in IVF patients undergoing COH who have a bodyweight of more than 75 kg. In addition, daily subcutaneous administration of cetrorelix at a daily dosage of 2.0 mg (with or without 400 I.U. recLH) is well-tolerated and shows no apparent adverse effects in women undergoing COH and subsequent IVF and ET.

Example 2

Oocytes are retrieved from the human females that have undergone COH as set forth in example 1. The oocytes are subsequently fertilized in vitro and two days later no more than two embryos are transferred to the uterus of the patient. In order of magnitude, the highest implantation and pregnancy rates are obtained in IVF-patients, in whom premature LH surges are prevented by a daily dosage of a combination of 2.0 mg cetrorelix and 400 IU recLH. Lower implantation and pregnancy rates are obtained in IVF-patients, in whom premature LH surges are prevented by a daily dose of 0.25 mg cetrorelix. Finally, lowest implantation and pregnancy rates are obtained in IVF-patients, in whom premature LH surges are prevented by a daily dose of 2.0 mg cetrorelix (without co-administered recLH).

Example 3

Examples 1 and 2 are repeated using 2.0 mg ganirelix instead of 2.0 mg cetrorelix. The results obtained are very similar to those described in examples 1 and 2.

The invention claimed is:

1. A method of controlled ovarian hyperstimulation in a mammalian female, said method comprising the co-administration to said female of: a substance having follicle stimulating hormone activity (FSH substance) in an amount effective to stimulate multiple follicular development, said FSH substance selected from the group consisting of recombinant FSH (recFSH) and urinary FSH (uFSH); a gonadotropin releasing hormone (GnRH) antagonist in an amount equivalent to a daily subcutaneous dose of 1.0-4.0 mg ganirelix to prevent a premature LH-surge, said GnRH antagonist selected from the group consisting of ganirelix, cetrorelix, and mixtures thereof; and an LH substance being recombinant LH (recLH) in an amount equivalent to a daily subcutaneous dose of between 1 and 40 I.U. recLH per kg of bodyweight to prevent or supress symptoms of luteinising hormone (LH) deficiency resulting from the admistration of the GnRH antagonist; followed by the administration of a meiosis and luteinisation inducing substance (ML substance) in an amount effective to stimulate resumption of meiosis and luteinisation, said ML substance selected from the group consisting of recLH, urinary chorionic gonadotropin (uCG), recombinant CG, and mixtures thereof.

2. The method according to claim 1, wherein the LH substance is administered in an amount effective to maintain the females blood serum concentration of LH substance at a level equivalent to more than 1 I.U. LH/liter of blood serum.

3. The method according to claim 1, wherein the GnRH-antagonist is administered at least during the period starting with the moment when a largest developing ovarian follicle has reached an average diameter of 14 mm, and ending one day prior to the administration of the ML substance in an amount effective to stimulate resumption of meiosis and luteinisation.

4. The method according to claim 1, wherein the GnRH-antagonist is administered at least during the period commencing either 6 days after the start of administration of the FSH substance, or at least 4 days prior to the administration of the ML substance in an amount effective to stimulate resumption of meiosis and luteinisation, whichever is the earliest, and ending one day prior to said administration of the ML substance.

5. The method according to claim 1, wherein the LH substance is administered at least during the period commencing 2 days after the start of administration of the GnRH antagonist and ending with the discontinuation of the administration of the GnRH antagonist.

6. The method according to claim 1, wherein the FSH substance is administered at least during the period starting 8 days after the female's spontaneous menses until the day before administration of the ML substance in an amount effective to stimulate resumption of meiosis and luteinisation.

7. The method according to claim 1, wherein the LH substance used to prevent or suppress symptoms of LH deficiency is obtained from a recombinant cell line.

8. The method according to claim 1, wherein the FSH substance, the GnRH antagonist and the LH substance are administered at least once a day, preferably parenterally.

9. The method according to claim 1, wherein the LH substance is administered in an amount effective to maintain the females blood serum concentration of LH substances at a level equivalent to more than 1.2 I.U. LH/liter.

10. The method according to claim 1, wherein the LH substance is administered in a daily dose which is equivalent to an subcutaneous dose of between 2 and 15 I.U. recombinant LH per kg of bodyweight.

11. The method according to claim 1, wherein the GnRH-antagonist is administered at least during the period starting with the moment when a largest developing ovarian follicle has reached an average diameter of 12 mm and ending one day prior to the administration of the ML substance in an amount effective to stimulate resumption of meiosis and luteinisation.

12. The method according to claim 1, wherein the GnRH-antagonist is administered at least during the period starting with the moment when a largest developing ovarian follicle has reached an average diameter of 10 mm and ending one day prior to the administration of the ML substance in an amount effective to stimulate resumption of meiosis and luteinisation.

13. The method according to claim 1, wherein the FSH substance is administered at least during the period starting 6 days after the female's spontaneous menses until the day before administration of the ML substance in an amount effective to stimulate resumption of meiosis and luteinisation.

* * * * *